United States Patent [19]
Marchesi

[11] Patent Number: 6,165,134
[45] Date of Patent: Dec. 26, 2000

[54] APPARATUS FOR FACILITATING RESPIRATORY RHYTHM CONTROL

[76] Inventor: Fabio Paolo Marchesi, Via Tadino, 13, 20124 Milan, Italy

[21] Appl. No.: 09/362,137

[22] Filed: Jul. 28, 1999

[30] Foreign Application Priority Data

Aug. 5, 1998 [IT] Italy ................................ MI98A1840

[51] Int. Cl.⁷ ..................................... A61B 5/08
[52] U.S. Cl. .......................... 600/529; 600/513
[58] Field of Search .................... 600/529–543, 600/508, 509, 513; 128/204.23

[56] References Cited

U.S. PATENT DOCUMENTS

| 4,519,395 | 5/1985 | Hrushesky . | |
|---|---|---|---|
| 5,377,671 | 1/1995 | Biondi et al. | 128/204.23 |
| 5,740,797 | 4/1998 | Dickson | 128/204.28 |
| 5,803,870 | 9/1998 | Buhler | 482/8 |
| 6,079,412 | 6/2000 | Meier et al. | 128/204.23 |

FOREIGN PATENT DOCUMENTS

| 2315332 | 1/1998 | United Kingdom . |
|---|---|---|
| WO96/20639 | 7/1996 | WIPO . |

OTHER PUBLICATIONS

Alamsi et al. "Basic Technology Of Voluntary Cardiorespiratory Synchronization In Electrocardiology".

Wang L. et al. "Respiratory Effects On Cardiac Related Impedance Indices Measured Under Vuluntary Cardio–Respiratory Synchronisation (VCRS)".

*Primary Examiner*—Cary O'Connor
*Assistant Examiner*—Navin Natnithithadha
*Attorney, Agent, or Firm*—Shlesinger, Fitzsimmons & Shlesinger

[57] ABSTRACT

An apparatus for controlled regulation of respiration depending on heart rate, in which the inspiration phase has a duration corresponding to a first multiple of the heartbeat period and the expiration phase has a duration corresponding to a second multiple of the heartbeat period, comprises a unit for heartbeat detection (14), a calculation unit (12) for processing data relative to heartbeat depending on external parameters and producing output signals which are a function of said multiples and external parameters, and signalling means (15) adapted to constitute a guide for the inspiration and expiration phases, piloted by said output signals. The apparatus may further comprise a respiration detecting unit (19), connected to the calculation unit (12) for comparison between the real respiration and theoretical respiration calculated by the calculation unit (12).

10 Claims, 1 Drawing Sheet

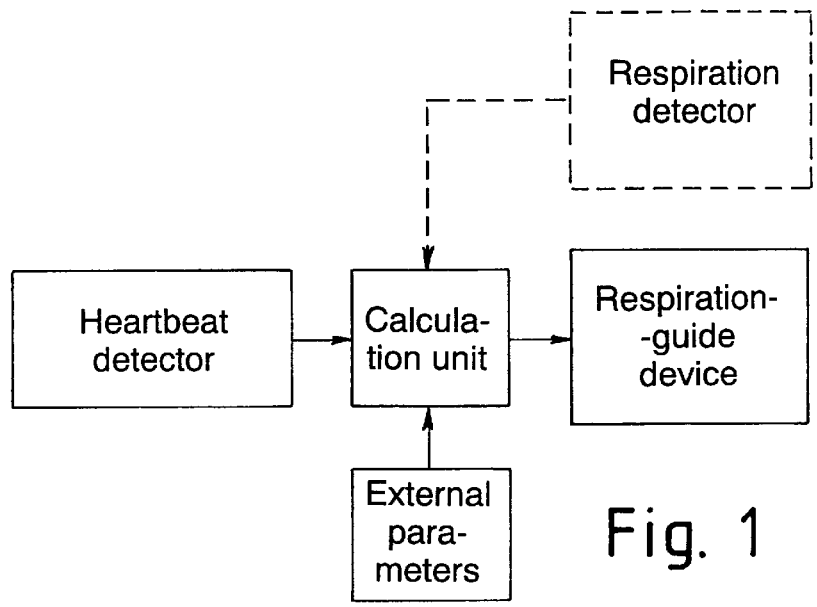
Fig. 1
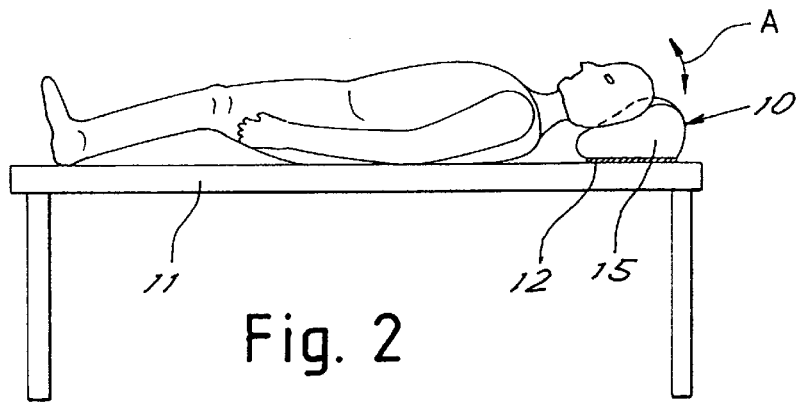
Fig. 2
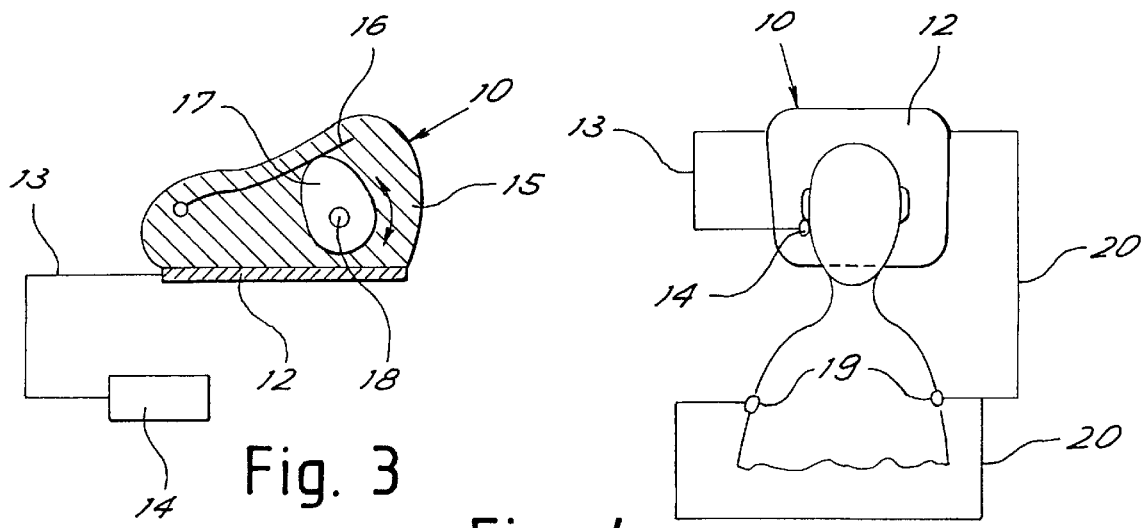
Fig. 3
Fig. 4

APPARATUS FOR FACILITATING RESPIRATORY RHYTHM CONTROL

BACKGROUND OF THE INVENTION

The present invention relates to an apparatus for control and optimization of the respiratory function in a human body.

It is known that a human organism is capable of giving best performance from the point of view of physical efficiency as well as in terms of relaxation and concentration, when respiration is carried out following rhythms which are as much as possible regular. A typical example of these techniques involves regulation of the respiratory phases depending on time references, carrying out an inspiration every $n_1$ seconds and an expiration every $n_2$ seconds, for example.

Such a control of the respiratory rhythm however does not give quite satisfactory results, because actually there are other physiologic parameters affecting the organism functions. In particular, it has been found that surprising results, both in terms of physical performance of a subject submitted to an effort, and in terms of relaxation and concentration of a subject at rest, are achieved by coordinating the respiratory rhythm with the heart rate (i.e. using as a measurement unit for respiration the heartbeat period).

Heart rate is an involuntary physiologic function, varying in time depending on emotional conditions and the physical efforts performed by a subject and it is difficult for a normal person to have sufficient sensitiveness of his/her heart rate to enable him/her to give a particular rhythm to respiration based on said heart rate.

It is a general object of the present invention to provide an apparatus allowing a controlled regulation of respiration, in order to optimize the physiologic functions of an organism.

SUMMARY OF THE INVENTION

In view of the above object, in accordance with the invention an apparatus has been conceived for controlled regulation of respiration in a subject depending on heart rate, in which the inspiration phase has a duration corresponding to a first multiple of the heartbeat period and the expiration phase has a duration corresponding to a second multiple of the heartbeat period of the same subject, comprising a unit for heartbeat detection, a calculation unit for processing data relative to heartbeat depending on external parameters and producing output signals, which are a function of said multiples and external parameters, piloting signalling means adapted to constitute a guide for the inspiration and expiration phases.

BRIEF DESCRIPTION OF THE DRAWINGS

For better explaining the innovatory principles of the present invention and the advantages it offers over the known art, a possible embodiment of the invention applying these principles will be given hereinafter, by way of non limiting example, with the aid of the accompanying drawings. In the drawings:

FIG. 1 is a block diagram of the system for controlled regulation of the respiratory rhythm in accordance with the invention.

FIG. 2 is a diagrammatic view of an apparatus for controlled regulation of the respiratory rhythm using the innovatory principles of the invention.

FIG. 3 is a sectional view in detail of the apparatus shown in FIG. 2.

FIG. 4 is an operation diagram of the apparatus in FIG. 2.

DETAILED DESCRIPTION OF THE INVENTION

As viewed from the block diagram in FIG. 1, the system for controlled regulation of the respiratory function in accordance with the invention comprises a calculation unit arranged to receive data relative to heart rate, which is transmitted from a heartbeat detector, suitably applied to the user's body.

The system for regulation of the respiratory rhythm in accordance with the invention further comprises a respiration guide device or respiration stimulator, controlled by output signals of the calculation unit, to signal execution times and modalities of the inspiration and expiration phases to the user.

Data processing carried out by the calculation unit advantageously takes place also depending on external parameters, that can vary depending on the user's physical features, the application conditions (at rest or under stress), the desired ratio to be maintained between duration of the inspiratory phase and duration of the expiratory phase, etc.

For instance, satisfactory results have been obtained by maintaining the inspiratory phase equal to two heartbeats and the expiratory phase equal to three heartbeats. In this case the multiple (2 and 3) value is entered into the calculation unit, by means of a keyboard for example, so as to obtain an output signal having as the time unit the heartbeat period and the cycle of which is determined by the entered multiples.

At all events, as said, these values are only given as an indication, as they can vary depending on the subject's features and the application conditions of the treatment. The system for controlled regulation of the respiratory rhythm in accordance with the invention may optionally comprise a detector for user's respiration, so that data relative to the actual respiration rate of the person being submitted to treatment is sent to the calculation unit. If the actual respiration rate is different from the optimal one provided by the calculation unit and signalled by the respiration signalling means, the calculation unit can process a transitory phase (having a duration of some minutes) during which the guided-respiration rhythm is gradually led to come close to the optimal rhythm, starting from the detected one.

Alternatively, display means showing deviation of the detected cycle from the desired cycle may be provided, to enable the subject to adapt the first one to the second one.

Shown in FIG. 2 is an embodiment of an apparatus (generally identified by 10) using the operation principles described in the diagram in FIG. 1. Apparatus 10 is made, in terms of construction, like a head support for the subject to be submitted to treatment, advantageously applicable to an examination couch or a bed 11.

As clearly shown in FIGS. 3 and 4 too, apparatus 10 comprises a calculation unit 12 connected, by an electric conductor 13, to a heartbeat detector 14. The heart rate detector herein shown is advantageously formed of a sensor placed behind the user's ear to detect the blood flow through measurement of the light-absorption variations at this body area. Obviously, for the purpose other known devices may be also used, based on measurement of the electric conductivity, as well as optical or acoustic measurement devices, possibly applied to other body parts. Apparatus 10 further comprises a stimulator 15 for the respiratory rhythm (constituting an example of a respiration-guide device shown in FIG. 1), controlled by the calculation unit 12. Stimulator 15 is intended for signalling to the user when he/she must inspire and expire, stimulating these functions by determining the body position promoting respiration.

In the embodiment shown, stimulator 15 is made up of a cushion of variable thickness herein diagrammatically illustrated as comprising an oscillating frame 16, operated by rotation of a cam 17 around a spindle 18 connected to an electric motor not shown.

Rotation of cam 17 alternately causes raising and lowering of the cushion rest surface (as shown by arrow A in FIG. 2) between the lowered position shown in solid line and the raised position shown in chain line. In particular, cushion lowering signals the inspiration phase to the user, whereas cushion raising signals the expiration phase to him/her, guiding the natural head movement following thorax expansion and contraction during execution of the respiratory phases. The instantaneous cam speed is piloted by the signal produced by the calculation unit.

Also diagrammatically shown in FIG. 4 is a respiration detector 19 that may consist either of electrodes, photocouplers, optical or acoustic sensors placed on the user's thorax or back, or of mechanical or electromechanical detectors placed at the user's nose or mouth to measure the inspired and expired air flow. Detector 19 is connected, via an electric conductor 20, to the calculation unit 12 to supply the latter with the measured values, for carrying out a comparison between the theoretical respiration data and the actual respiration data and execute a possible transitory phase for approaching the real respiration to the optimal one.

At this point it is apparent how the system for controlled regulation of the respiratory rhythm in accordance with the invention achieves the intended purposes.

Obviously, the system for regulation of the respiratory function can be applied to apparatus of various types, having different construction features depending on the use for which they are intended and the modalities for signalling and guiding the respiratory phases.

Connections between the calculation unit and respiration and heartbeat detecting devices can be made by telemetering, instead of using electric connections.

The stimulator guiding the respiration rhythm can be limited to emission of a tactile, visual or acoustic signal constituting the only signalling element to which the subject must react for regulating his/her respiratory rhythm. It may also comprise an actuator element applying a direct physical action to the user's body, capable of promoting movement causing inspiration and expiration.

What is claimed is:

1. An apparatus for controlled regulation of respiration in a subject depending on heart rate, in which the inspiration phase has a duration corresponding to a first multiple of the heartbeat period and the expiration phase has a duration corresponding to a second multiple of the heartbeat period of the same subject, comprising a unit for heartbeat detection, a calculation unit for processing data relative to heartbeat depending on external parameters and producing output signals, which are a function of said multiples and external parameters, piloting signalling means adapted to constitute a guide for the inspiration and expiration phases.

2. An apparatus as claimed in claim 1, characterized in that the signalling means is perceptible by the subject.

3. An apparatus as claimed in claim 1, characterized in that the signalling means is piloted to cause movement of the subject's body, so as to alternately promote inspiration and expiration.

4. An apparatus as claimed in claim 1, characterized in that the signalling means signals at least the beginning of the inspiration and expirations phases.

5. An apparatus as claimed in claim 1, characterized in that it comprises a respiration-detecting unit connected to the calculation unit for comparison between the real respiration and the desired theoretical respiration, calculated by the calculation unit.

6. An apparatus as claimed in claim 5, characterized in that the output signals of the calculation unit pilot a progressive approaching of the real respiration rhythm to the desired theoretical respiration rhythm.

7. An apparatus as claimed in claim 5, characterized in that the respiration detecting unit is made up of sensors to be positioned at the thorax.

8. An apparatus as claimed in claim 1, characterized in that the signalling means comprises a support for the user's head, controlled by the output signal of the calculation unit so that it lowers during the inspiration phase and rises during the expiration phase, thereby accompanying the head in the natural movement imparted to it by thorax expansion and contraction.

9. An apparatus as claimed in claim 8, characterized in that the support is a cushion provided with an oscillating frame swinging between said raised and lowered positions, being operated by rotation of a cam.

10. An apparatus as claimed in claim 1, characterized in that the heartbeat detecting unit is made up of a sensor to be positioned behind the user's ear to measure his/her blood flow.

* * * * *